US011103180B2

(12) United States Patent
Grashow

(10) Patent No.: US 11,103,180 B2
(45) Date of Patent: Aug. 31, 2021

(54) ADVICE SYSTEM STRUCTURED TO IDENTIFY AN APPROPRIATE MEDICAL DEVICE BASED UPON GENETIC ANALYSIS

(71) Applicant: KONINKLIJKE PHILIPS N.V., Eindhoven (NL)

(72) Inventor: Jonathan Sayer Grashow, Cheswick, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1236 days.

(21) Appl. No.: 15/105,616

(22) PCT Filed: Dec. 18, 2014

(86) PCT No.: PCT/IB2014/067051
§ 371 (c)(1),
(2) Date: Jun. 17, 2016

(87) PCT Pub. No.: WO2015/092724
PCT Pub. Date: Jun. 25, 2015

(65) Prior Publication Data
US 2016/0321429 A1    Nov. 3, 2016

Related U.S. Application Data

(60) Provisional application No. 61/918,805, filed on Dec. 20, 2013.

(51) Int. Cl.
| | |
|---|---|
| *G01N 33/48* | (2006.01) |
| *G01N 33/50* | (2006.01) |
| *A61B 5/00* | (2006.01) |
| *G16H 50/20* | (2018.01) |
| *A61M 16/06* | (2006.01) |
| *G16H 20/30* | (2018.01) |
| *G06N 5/04* | (2006.01) |
| *G06N 7/00* | (2006.01) |

(52) U.S. Cl.
CPC ....... *A61B 5/4818* (2013.01); *A61M 16/0605* (2014.02); *G06N 5/04* (2013.01); *G06N 7/005* (2013.01); *G16H 20/30* (2018.01); *G16H 50/20* (2018.01); *A61M 2016/0661* (2013.01); *A61M 2207/00* (2013.01)

(58) Field of Classification Search
CPC ...... A61B 5/4818; G16H 20/30; G16H 50/20; G06N 5/04; G06N 7/005; A61M 16/0605; A61M 2207/00; A61M 2016/0661
See application file for complete search history.

(56) References Cited

U.S. PATENT DOCUMENTS

| | | | |
|---|---|---|---|
| 8,276,588 B1 * | 10/2012 | Connor | A61M 16/06 128/205.25 |
| 2007/0015837 A1 * | 1/2007 | Kun | A61K 31/165 514/621 |
| 2008/0060652 A1 | 3/2008 | Selvarajan | |
| 2012/0321759 A1 | 12/2012 | Marinkovich | |

FOREIGN PATENT DOCUMENTS

| | | | | |
|---|---|---|---|---|
| EP | 2428241 A1 | 3/2012 | | |
| EP | 2504813 A1 * | 10/2012 | ........... | G06T 3/0093 |
| WO | WO2013001438 A1 | 1/2013 | | |
| WO | WO2013183018 A1 | 12/2013 | | |

OTHER PUBLICATIONS

Stacey, Michael C. et al., "Genetic Polymorphisms May Influence the Development and Healing of Sitting-Acquired Pressure Ulcers Following Spinal Cord Injury", Top Spinal Cord Inj Rehabil. 2012 Spring; 18(2): 132-134.
"Are Telomeres the Key to Aging and Cancer?", webpage—no date http://learn.genetics.utah.edu/content/begin/traits/telomeres/.
DNA Assessments—GeneLink BioSciences, webpage—no date http://dermagenetics.com/dna-assessments/.

\* cited by examiner

*Primary Examiner* — Russell S Negin
(74) *Attorney, Agent, or Firm* — Michael W. Haas

(57) ABSTRACT

An advice system employs a genetic analysis of a patient to identify one or more characteristics of the patient. The advice system employs the characteristics to identify one or more attributes of a medical device that would desirably exist in a medical device that is to be prescribed for the patient. The advice system then identifies from the one or more attributes one or more medical devices from among a plurality of medical devices whose features at least in part meet the one or more attributes. The advice system then outputs a recommendation of the one or more medical devices. The system employs known genes that are expressive of certain traits in a person, with the known traits being interpreted or evaluated in terms of characteristics that are relevant in selecting a medical device from among a plurality of medical devices, such as patient interface devices or other devices.

20 Claims, 2 Drawing Sheets

ADVICE SYSTEM STRUCTURED TO IDENTIFY AN APPROPRIATE MEDICAL DEVICE BASED UPON GENETIC ANALYSIS

CROSS-REFERENCE TO RELATED APPLICATIONS

This patent application claims the priority benefit under 35 U.S.C. § 371 of international patent application no. PCT/IB2014/067051, filed Dec. 18, 2014, which claims the priority benefit under 35 U.S.C. § 119(e) of U.S. Provisional Application No. 61/918,805 filed on Dec. 20, 2013, the contents of which are herein incorporated by reference.

BACKGROUND OF THE INVENTION

1. Field of the Invention

The disclosed and claimed concept relates generally to medical devices that provide respiratory therapy or other therapy to a patient and, more particularly, to a system that employs genetic information from a patient to identify desirable medical devices that are appropriate for the patient.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 times per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Non-invasive respiratory therapies such as ventilation and pressure support therapies involve the placement of a patient interface device, which is typically a nasal or nasal/oral mask, on the face of a patient to interface a source of breathing gas such as a ventilator or pressure support system in fluid communication with the airway of the patient so that a flow of breathing gas can be delivered from the pressure/flow generating device to the airway of the patient.

Typically, patient interface devices include a mask shell or frame having a cushion attached to the shell that contacts the skin of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Numerous situations exist wherein it is necessary or desirable to deliver a flow of breathable gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as sleep apnea syndrome, in particular, obstructive sleep apnea (OSA), or congestive heart failure.

No two patients are exactly alike. As such, numerous different patient interface devices having numerous different features such as various shapes, materials, configurations, and the like exist and are selectable for a patient based upon fit and other appropriate criteria. Due to the wide variety of features in the various masks and the inability to always know all of the characteristics of the patient that are relevant to the selection of a patient interface device, difficulty has been experienced in identifying what are the most appropriate patient interface devices based upon all of the various patient characteristics.

SUMMARY OF THE INVENTION

An improved advice system is configured to employ a genetic analysis of a patient to identify one or more characteristics of the patient. The advice system employs the characteristics to identify one or more attributes of a medical device that would desirably exist in a medical device that is to be prescribed for the patient. The advice system then identifies from the one or more attributes one or more medical devices from among a plurality of medical devices whose features at least in part meet the one or more attributes. The advice system then outputs a recommendation of the one or more medical devices. The system employs known genes that are expressive of certain traits in a person, with the known traits being interpreted or evaluated in terms of characteristics that are relevant in selecting a medical device from among a plurality of medical devices, such as patient interface devices or other devices.

Accordingly, an aspect of the disclosed and claimed concept is to provide an improved method of recommending a medical device from among a plurality of medical devices based upon a genetic analysis of the patient.

Another aspect of the disclosed and claimed concept is to identify from the genetic analysis one or more characteristics of the patient and to, in turn, identify from the one or more characteristics one or more attributes that would be desirable in a medical device for the patient.

Another aspect of the disclosed and claimed concept is to identify a medical device from among a plurality of medical devices that optimally or at least in part meets the one or more attributes and outputs a recommendation of the medical device for the patient.

Another aspect of the disclosed and claimed concept is to provide an improved advice system for recommending a medical device such as a patient interface device for providing respiratory therapy to a patient.

Accordingly, an aspect of the disclosed and claimed concept is to provide an improved method of recommending at least one medical device from among a plurality of medical devices as being desirable for a patient, with each medical device of the plurality of medical devices having one or more features. The method can be generally stated as including identifying at least in part from a genetic analysis of the patient one or more characteristics of the patient, identifying at least in part from the one or more characteristics of the patient one or more attributes that would be desirable in a medical device of the plurality of medical devices for the patient, identifying at least in part from the one or more attributes one or more medical devices from among the plurality of medical devices whose features at least in part meet at least a portion of the one or more attributes, and outputting a recommendation of at least one medical device from among the one or more medical devices.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
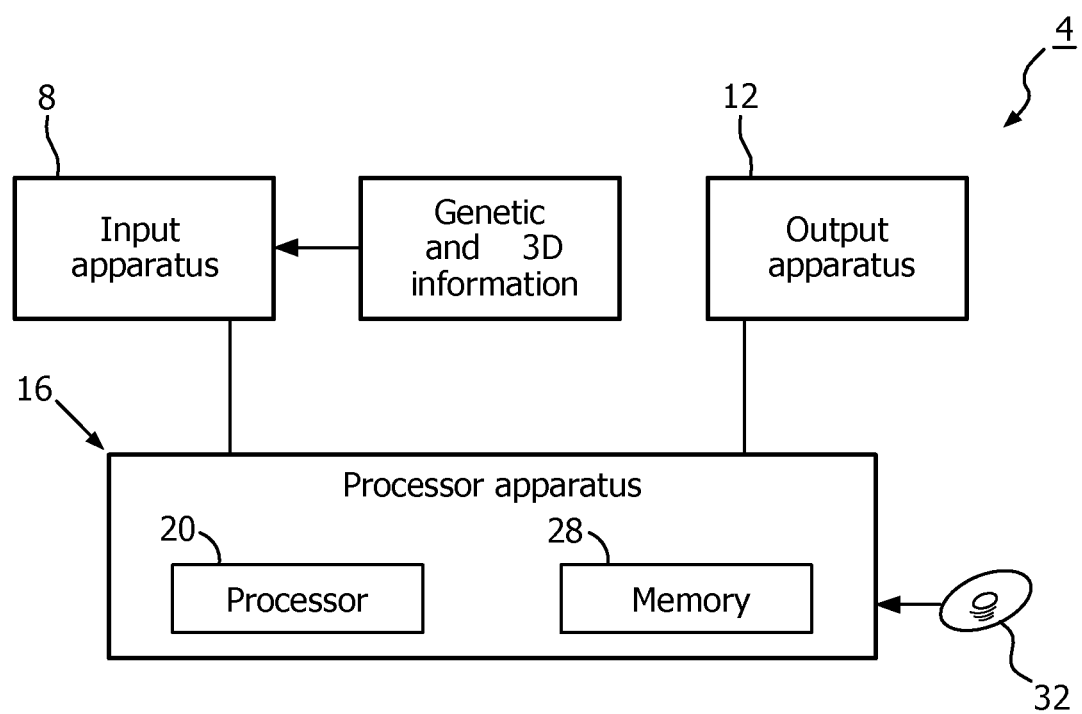
FIG. 1 is schematic depiction of an improved advice system in accordance with the disclosed and claimed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

An improved advice system 4 in accordance with the disclosed and claimed concept is depicted generally in FIG. 1. The improved advice system 4 can be said to be operable to provide, from among a plurality of medical devices, a recommendation of a particular medical device or a small number of medical devices that are especially suited to a patient based at least in part upon a genetic analysis of the patient's DNA. For example, the patient may submit a DNA sample for analysis or may grant access to a preexisting set of genetic information for the patient, although other systems and methodologies for obtaining, generating and using genetic information regarding the patient that are in accordance with the disclosed and claimed concept will be apparent to one of ordinary skill in the relevant art. In the depicted examples presented herein, the medical device that is recommended by advice system 4 is in the exemplary form of a patient interface device that is configured to provide respiratory therapy to a patient, such as a CPAP mask or other type of patient interface device. It is understood, however, that the teachings herein are not intended to be limited to such patient interface devices and rather are applicable to all types of medical devices and other devices that selected for use with a patient or other individual.

The exemplary advice system 4 can be said to include in input apparatus 8, an output apparatus 12, and a processor apparatus 16. Input apparatus 8 can be any of a wide variety of input devices that might include, for example and without limitation, keyboards, CD ROM readers, electronic data interfaces that follow any of a variety of known protocols such as Small Computer Systems Interface (SCSI), IEEE 802.11, Ethernet, and the like, as well as other input devices, all of which are configured to provide input signals to processor apparatus 16. Output apparatus 12 can be any of a wide variety of devices and may include, for example, video displays, printers, data interfaces such as those set forth in the preceding sentence, and other output devices that all receive output signals from processor apparatus 16.

Processor apparatus 16 in the depicted exemplary embodiment includes a processor 20 and a memory 24 that are in communication with one another. Processor 20 can be any of a wide variety of processors such as, for example and without limitation, a microprocessor or other processor or a bank of processing capability, etc., without limitation. Memory 24 can be any of a wide variety of storage devices and may include RAM, ROM, EPROM, EEPROM, FLASH, and the like without limitation. Memory 24 has stored therein a set of instructions 28 that are generally in the form of routines or other types of instructions which, when executed on processor 20, cause advice system 4 to perform certain predetermined functions. Instructions 28 can also be stored on a non-transitory machine-readable storage medium 32 which is depicted as being in the exemplary form of a CD ROM that is employed to place instructions 28 into memory 24, although it is understood that memory 24 can itself constitute such a non-transitory machine-readable storage medium. Other variations will be apparent to one of ordinary skill in the art.

Figure 2:
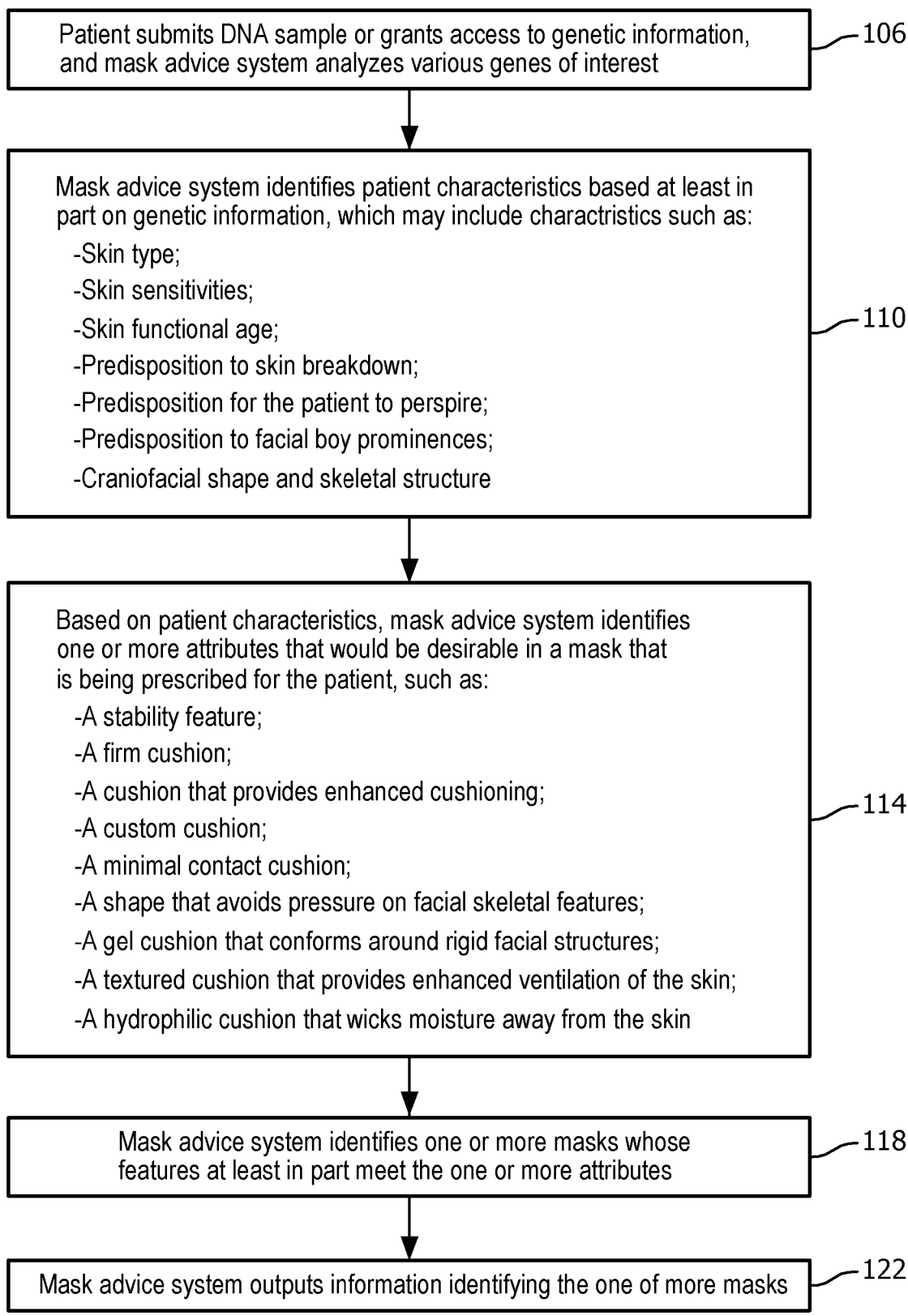
FIG. 2 is a flowchart depicting certain aspects of an improved method in accordance with the disclosed and claimed concept.

Certain operations of advice system 4 are described below in conjunction with an exemplary flowchart that is depicted generally in FIG. 2. A patient submits a DNA sample or grants access to genetic information, as at 106 and advice system 4 analyzes various genes of interest. As is generally understood, the genetic information may be represented by a string or chain of letters, with such letters each representing a nucleotide, and with the various chains of nucleotides being obtained from the patient's DNA. The genetic information can take any of a wide variety of other forms, some of which are set forth in greater detail below, without departing from the present concept.

Advice system 4 then employs the genetic information and identifies, as at 110, one or more patient characteristics that are based at least in part on the genetic information. In this regard, certain genes are expressive in a known fashion of certain physical traits of the person or patient whose DNA is under analysis. For instance, the known MMP1 gene is expressive of a trait of excessive generation of the enzymes interstitial collagenase and/or fibroblast collagenase. It is noted that the trait of excessive generation of such enzymes is associated with skin and other tissue breakdown. Such trait of excessive generation of interstitial collagenase and/or fibroblast collagenase can be said to exist in a person whose MMP1 gene is the subject of a single nucleotide polymorphism. It thus can be seen that genetic information in the form of a detection of a single nucleotide polymorphism in the MMP1 gene is usable to discern a physical trait in the patient in the form of excessive generation of interstitial collagenase and/or fibroblast collagenase.

Advantageously, advice system 4 employs or interprets the genetic information and/or the identified physical trait, or both, to identify a characteristic of the patient that is relevant to the medical device in question which, in the depicted exemplary embodiment, is a CPAP mask. More particularly, advice system 4 in the depicted exemplary embodiment identifies from the aforementioned physical trait of the patient a characteristic of the patient in the form of a predisposition to skin breakdown. Such a characteristic is relevant to the use of a CPAP mask since such a medical device typically is physically engaged with the face of the patient for extended periods of time, such as during normal sleep periods.

Other aspects of the genetic information are relevant to identify other physical traits or other traits of the patient that can be identified by the advice system 4 as other characteristics of the patient. Such other characteristics can include, by way of example, a skin type, certain skin sensitivities, skin functional age, a predisposition for the patient to perspire, a predisposition for the patient to have facial bony prominences, and certain aspects of the craniofacial shape and skeletal structure of the patient, by way of example. For instance, the skin type might be discerned as being generally oily, dry, or as having other characteristics. By way of further example, the functional age of the skin might be determined based upon an observed shortening in the length of the telomeres, it being understood that such shortening of the telomeres is indicative of excessive DNA replication. An identified trait in the form of a patient's functional age well in excess of the patient's chronological age might indicate a characteristic that the patient's skin is loose or wrinkled, i.e., as lacking in elasticity. Still other characteristics of the patient that are not expressly set forth herein may be obtained from the genetic information.

It is understood that the genetic information need not be limited to instances of mutation, i.e., nucleotide polymorphism, but rather can be obtained from any type of data that can be discerned from the genetic information. For example, the aforementioned identified shortening of the length of the telomeres can be indicative of a functional age that is in excess of the patient's chronological age. Another example of such genetic data is in the various alleles of known genes. For example, one allele of a known gene is expressive for blue eyes whereas another allele of the same gene is expressive for brown eyes. Such alleles and their genes need not be the subject of mutation in order to be relevant to advice system 4. Other alleles of a known gene may be expressive of oily skin or dry skin or sensitive skin, by way of example.

Once advice system 4 has identified the various characteristics such as physical characteristics of the patient that are relevant to the type of medical device that is being considered for the patient, advice system 4 identifies, as at 114, one or more attributes of a medical device would be desirable for the patient based upon the patient's characteristics, i.e., those identified at 110. For example, in a situation wherein the patient is determined to have as a characteristic a likelihood of skin that is loose or wrinkled or that is lacking in elasticity, advice system 4 might identify as an attribute that would be desirable in a mask a stability feature such as a forehead pad that would hold the mask in place despite loose skin. Another example of an identified desirable attribute of a mask is such a situation may be a firm cushion that can push into and seal against wrinkled skin.

Similarly, an identification of a patient characteristic in the form of a predisposition for skin breakdown might cause advice system 4 to identify as attributes of a mask that would be desirable for the patient a minimal contact mask such as a nasal pillows mask or other such mask that imparts reduced contact forces or that makes contact with minimal areas of the skin or both. Alternatively or additionally, advice system 4 might identify as an attribute a custom cushion that might provide a better fit and avoid pressure points. Another attribute in such a situation may be a liquid-containing cushion such as a LiquiCell nasal CPAP cushion of the type offered by Birchwood Laboratories, Inc. of Eden Prairie, Minn. 55344, or other type of cushion that provides an enhanced cushioning function.

If advice system 4 identifies from the genetic data and/or other data an existence of a predisposition for facial bony prominences in the patient, advice system 4 might identify as desirable attributes a mask having a shape that avoids pressure on facial skeletal features and/or a gel cushion that confirms around rigid facial structures, by way of example. Furthermore, another attribute might be a custom mask that optimizes contact with one or more specific bony prominences. For example, a custom mask might generally match the skin surface, but would be designed to have some amount (e.g. 5 mm) of planned interference with the skin to create a robust seal. To further improve the design of this custom mask at locations where the patient is likely to have bony prominences, this planned interference might be reduced (e.g. to 2 mm) in order to prevent excessive pressure from being applied to the skin between the bony prominence and the mask.

A 3D scan of the patient's skin may be employed in addition to the genetic information to identify and develop attributes of a preexisting mask or a custom mask. For instance, id a patient is likely to have specific bony prominences, then a technician or medical professional can estimate the underlying skeletal structure and create a mask (or other device) that provides a custom fit to the patient's skeleton. In some cases, such a custom fit may be better than a custom fit to the patient's skin surface.

These and other desirable attributes might also be identified based upon a determination of the craniofacial shape and/or the patient's skeletal structure. Either may be derived from the genetic information or other information.

By way of further example, if advice system 4 determines that a patient has a characteristic of a predisposition to perspire, advice system 4 might identify as desirable attributes a textured cushion that provides enhanced ventilation of the skin and/or a hydrophilic cushion that wicks moisture away from the skin. Other types of attributes might also be identified by advice system 4 in the event that the patient is determined to have a predisposition to perspire or to have other characteristics.

It is also noted that information regarding the patient's race, whether derived genetically or otherwise, can also be employed in identifying certain attributes that may be desirable in a medical device. For instance, features related to the patient's jaw, forehead, mouth, cheeks, nose, ears, or other body part that is based at least in part upon the patient's race might cause advice system 4 to identify other attributes that would be desirable or appropriate in a CPAP mask or other medical device.

Advice system then identifies, as at 118, one or more masks whose features at least in part meet one of more of the identified attributes. That is, advice system 4 would include data regarding the various features of all of the various CPAP masks or other medical devices that are available for selection. Advice system 4 would correlate the identified desirable attributes that would be appropriate for a mask that is intended to be used on the patient with the various features of the various masks in order to identify one particular mask or a small number of masks that have the greatest correlation between their features and the identified attributes in order to identify an optimum mask. In this regard, it is possible that advice system 4 may be configured to output additional data such as confidence values that are representative of the degree of correlation between the various masks that are identified and the various attributes, or other data, in order to enable a medical professional to make a better informed choice as to which individual mask from among the identified small number of masks is most ideally suited to the patient.

Advice system then outputs, as at 122, on the output apparatus 12 the identities of the one or more identified masks or other medical devices that have been identified as being especially appropriate or desirable for the patient. Output apparatus 12 may additionally output the other information mentioned above such as confidence data and other data that might enable a medical professional to choose from among the identified desirable masks a particular mask that is most ideally desirable for the patient.

It is understood that numerous other types of data in addition to the aforementioned genetic data can be employed to identify characteristics of a patient that are employable in identifying attributes of desirable medical devices in order to identify medical devices that are most ideally suited to a patient. It is also understood that the aforementioned physical traits and the characteristics of patients that are set forth above are merely exemplary in nature and are not intended to be limiting.

It is contemplated that any of the embodiments, combination of embodiments, or modification of embodiments of the disclosed concept described herein can be used by, for example and without limitation, a caregiver or technician, in the process of selecting a patient interface device for a patient.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of recommending at least one patient interface device from among a plurality of patient interface devices as being suited to provide treatment in the form of respiratory therapy to a patient, each patient interface device of the plurality of patient interface devices having one or more features, the method comprising:
    identifying (110) at least in part from a genetic analysis of the patient's DNA one or more characteristics of the patient;
    identifying (114) at least in part from the one or more characteristics of the patient one or more attributes that would be desirable in a patient interface device of the plurality of patient interface devices to provide treatment in the form of respiratory therapy to the patient;
    identifying (116) at least in part from the one or more attributes one or more patient interface devices from among the plurality of patient interface devices whose features at least in part meet at least a portion of the one or more attributes; and
    outputting (122) a recommendation to provide treatment in the form of treating the patient with respiratory therapy using at least one patient interface device from among the one or more patient interface devices.

2. The method of claim 1, further comprising identifying as at least a first characteristic of the one or more characteristics a characteristic related to at least one of:
    the patient's skin: and
    the patient's skeletal structure.

3. The method of claim 2, further comprising detecting from the genetic analysis a shortened length of a telomere in a strand of genetic material and, responsive at least in part thereto, identifying as the characteristic related to the patient's skin a characteristic associated with an increased functional age.

4. The method of claim 3, further comprising identifying, based at least in part upon the increased functional age of the patient's skin, as at least a first attribute of the one or more attributes a stability feature that is structured to hold a medical device of the plurality of medical devices in place on the patient's skin despite the skin being loose.

5. The method of claim 3, further comprising identifying, based at least in part upon the increased functional age of the patient's skin, as at least a first attribute of the one or more attributes a firm cushion that is structured to push into and seal against wrinkled skin.

6. The method of claim 2, further comprising detecting from the genetic analysis a mutation of a predetermined gene and, responsive at least in part thereto, identifying as the characteristic related to the patient's skin a characteristic associated with an increased level of skin breakdown.

7. The method of claim 6, further comprising identifying, based at least in part upon the increased level of skin breakdown, as at least a first attribute of the one or more attributes an enhanced cushioning feature.

8. The method of claim 6, further comprising identifying, based at least in part upon the increased level of skin breakdown, as at least a first attribute of the one or more attributes a custom cushion.

9. The method of claim 2, further comprising identifying as the at least first characteristic at least one of a mutation of a predetermined gene and an allele of a predetermined gene.

10. The method of claim 2, further comprising identifying as the at least first characteristic a predisposition for the patient to perspire.

11. The method of claim 10, further comprising identifying, based at least in part upon the predisposition for the patient to perspire, as at least a first attribute of the one or more attributes a textured cushion that is structure to provide enhanced ventilation of the patient's skin.

12. The method of claim 10, further comprising identifying, based at least in part upon the predisposition for the patient to perspire, as at least a first attribute of the one or more attributes a hydrophilic cushion that is structured to wick moisture away from the patient's skin.

13. The method of claim 2, further comprising identifying as the at least first characteristic a predisposition for the patient to have one or more bony prominences in the facial skeletal structure.

14. The method of claim 13, further comprising identifying, based at least in part upon the predisposition for the patient to have one or more bony prominences in the facial skeletal structure, as at least a first attribute of the one or more attributes a gel cushion that is structured to conform around rigid facial structures.

15. The method of claim 13, further comprising identifying, based at least in part upon the predisposition for the patient to have one or more bony prominences in the facial skeletal structure, as at least a first attribute of the one or more attributes one of:
- a medical device configured to avoid contact with one or more specific bony prominences, and
- a custom cushion structured to optimize contact with one or more specific bony prominences.

16. The method of claim 13, further comprising employing a 3D scan of the patient's skin surface in addition to the genetic analysis in the identifying of at least one attribute of the one or more attributes.

17. The method of claim 1, wherein the genetic analysis is based at least in part upon a DNA sample which the patient has submitted for analysis.

18. The method of claim 1, wherein the genetic analysis is based at least in part upon a preexisting set of genetic information for the patient to which the patient has granted access.

19. A machine structured to recommend at least one patient interface device from among a plurality of patient interface devices as being desirable to provide treatment in the form of respiratory therapy to a patient, each patient interface device of the plurality of patient interface devices having one or more features, the machine comprising:
- a processor apparatus comprising a processor and a memory;
- an input apparatus structured to provide input signals to the processor apparatus;
- an output apparatus structured to receive output signals to the processor apparatus;
- the memory having stored therein instructions which, when executed on the processor, cause the machine to perform operations comprising:
  - identifying at least in part from a genetic analysis of the patient's DNA one or more characteristics of the patient;
  - identifying at least in part from the one or more characteristics of the patient one or more attributes that would be desirable in a patient interface device of the plurality of patient interface devices to provide respiratory therapy to the patient;
  - identifying at least in part from the one or more attributes one or more patient interface devices from among the plurality of patient interface devices whose features at least in part meet at least a portion of the one or more attributes; and
  - outputting a recommendation to provide treatment in the form of treating the patient with respiratory therapy using at least one patient interface device from among the one or more patient interface devices.

20. A non-transitory machine-readable storage medium having stored thereon instructions which, when executed on a processor apparatus of a machine that is structured to recommend at least one patient interface device from among a plurality of patient interface devices as being desirable to provide respiratory therapy to a patient, each patient interface device of the plurality of patient interface devices having one or more features, cause the machine to perform operations comprising:
- identifying at least in part from a genetic analysis of the patient's DNA one or more characteristics of the patient;
- identifying at least in part from the one or more characteristics of the patient one or more attributes that would be desirable in a patient interface device of the plurality of patient interface devices to provide respiratory therapy to the patient;
- identifying at least in part from the one or more attributes one or more patient interface devices from among the plurality of patient interface devices whose features at least in part meet at least a portion of the one or more attributes; and
- outputting a recommendation to provide treatment in the form of treating the patient with respiratory therapy using at least one patient interface device from among the one or more patient interface devices.

\* \* \* \* \*